United States Patent [19]

Lorenz

[11] Patent Number: 5,741,702
[45] Date of Patent: Apr. 21, 1998

[54] SYSTEM FOR PROCESSING GASES CONTAINING CARBON DIOXIDE

[76] Inventor: Thomas Lorenz, Hansastr. 75, 49134, Wallenhorst-Hollage, Germany

[21] Appl. No.: 667,434

[22] Filed: Jun. 21, 1996

[30] Foreign Application Priority Data

Jun. 21, 1995 [DE] Germany .................. 195 22 429.9

[51] Int. Cl.[6] .................................................. C12M 3/00
[52] U.S. Cl. .................................................. 435/292.1
[58] Field of Search .................................................. 435/292.1

[56] References Cited

U.S. PATENT DOCUMENTS 4,868,123  9/1989  Berson et al. .................. 435/290

FOREIGN PATENT DOCUMENTS

| 2596-412 A | 3/1989 | France | C12M 1/02 |
| 2564-854 A | 5/1994 | France | C12M 1/02 |
| 3607864 A1 | 9/1986 | Germany | B01D 53/34 |
| WO 94/09113 | 4/1994 | WIPO | C12M 1/02 |

*Primary Examiner*—David A. Redding
*Attorney, Agent, or Firm*—Lahive & Cockfield, LLP

[57] ABSTRACT

In a system for processing gases containing carbon dioxide by means of a fluid containing algae, with a reactor vessel that can be illuminated and in which light energy is supplied to the algae, the invention proposes that the reactor vessel be designed as a plane element, with the plane element being made transparent to light on at least one of its two surfaces.

10 Claims, 1 Drawing Sheet

SYSTEM FOR PROCESSING GASES CONTAINING CARBON DIOXIDE

BACKGROUND OF THE INVENTION

The invention relates to a system for processing gases.

A conventional gas processing system is known from German Publication No. DE 36 07 864 A1. This document includes the statement that either diffuse sunlight or comparable light can be used as the energy source for the light energy. The nature of the design of the reactor vessel or the manner in which the light is introduced into the reactor vessel is not expressly mentioned in this publication. In any case, the individual skilled in the art is inspired by the drawing in this publication to install an electrical illuminator in the reactor vessel, since a corresponding symbol is shown in the reactor vessel.

With the introduction of light controlled in this fashion, the operating behavior of the entire system can be adjusted precisely to the quantity of exhaust fed into the fluid.

However, the known system suffers from the disadvantage that it takes up a great deal of space which must be provided in the form of a separate processing chamber.

In addition, it is known from practice to form a reactor vessel by using transparent pipes.

The arrangement of the pipes is serpentine or meander-shaped and requires a plurality of individual retaining elements, so that a considerable assembly expense unfavorably influences the cost of erecting such a system.

The goal of the invention is to improve a system according to the teachings of the present invention that can be built in a manner which is as economical of space as possible, ensuring rapid and simple installation of the piping system.

SUMMARY OF THE INVENTION

This goal according to the invention is achieved by the design as set forth below.

In other words, the invention proposes compressing the piping system at least section-wise into a plane element. Provision for the light to reach the algae from at least one side should be provided to ensure optimum working conditions for the algae.

First, use of a plane element permits optimum utilization of space since the fluid can be distributed over the entire surface of this plane element, while with a serpentine or meander-shaped arrangement of pipes, surface coverage is less favorable by comparison with a plane element closed in such fashion.

Second, installation of the piping system is much faster and simpler, since the sections designed as plane elements can be fastened together with fewer holders so that the number of fastening elements required is drastically reduced.

In contrast to a pot-shaped, three-dimensional reactor vessel, a reactor vessel that is designed to be primarily two-dimensional and in the form of a plane element, in practice, requires no significant erection area since the reactor vessel designed as a plane element can be mounted on walls, next to passageways like those found in company areas or buildings or the like. In other words theoretically, without taking up any space of their own.

Provision can advantageously be made to provide the plane element with a thermal insulating layer. In this manner, the application conditions for the algae can be made more uniform so that the efficiency of the system does not vary in degree with the outside weather conditions. In this manner, use of the reactor vessels in the open is facilitated or even made possible for the first time, depending on local weather conditions.

Thermal insulation evens out the temperature prevailing in the fluids, so that even at different external temperatures, the efficiency of the entire system is very uniform and reliable and adequate working results can be achieved. Provision can advantageously be made to design the plane element in three layers so that a middle fluid-conducting layer can be insulated from the two outer layers. In this fashion, the working conditions for the algae can be made more uniform.

The plane element design allows its use as an insulating panel on buildings, so that a compact system is created that does not require any additional mounting surfaces for these sections of the piping system.

The plane element can advantageously be designed as a ribbed plate. This design for plane elements, known of itself, permits economical manufacture while the plurality of ribs provided in one plane element confers high compressive strength on the entire plane element so that the thermally insulating layers can be evacuated by applying a vacuum, and optimum insulation results can be achieved.

A transparent or translucent material can advantageously be used for the ribbed plate. This makes the entire plane element permeable to light, so that it can be used, for example, in factory buildings instead of windows. These elements however are frequently not made transparent but translucent instead, so that by using the proposed plane elements, the visual conditions within the factory building are improved. Additional mounting locations for the piping system are therefore unnecessary so that the risk of damage to the piping system, like that which could occur on company property as a result of switching moves or the like, can be ruled out. By making the plane element of a single material, the plane element can be manufactured economically, for example, it can be extruded as a ribbed plate, so that a uniformly transparent or translucent design can produce a more economical plane element than a design with a light-blocking and a light-transparent side on the plane element.

The use of polycarbonate as a material permits a wear-resistant and very lightweight design for a plane element.

The insulating effect of the thermally insulating layers can advantageously be produced by an applied vacuum or by an applied reduced pressure. This results firstly in very low energy consumption since the vacuum, once created, merely needs to be maintained, so that the vacuum pumps must be switched on only intermittently. At the same time, an outstanding insulating effect is produced in the evacuated layers so that a considerable increase in efficiency for the operation of the algae can be produced. In particular, this efficiency can be maintained by constant maintenance of the vacuum, since leaks, for example by diffusion, cannot result in a gradual deterioration of the insulating effect, but are always compensated by the vacuum pumps that are connected.

Finally, a vacuum applied in this fashion permits rapid and reliable detection of leaks, since the fluid escaping from the fluid-carrying channels is conveyed through the evacuated layers with the aid of the vacuum pumps.

BRIEF DESCRIPTION OF THE DRAWINGS

One embodiment of a plane element like that which can be provided in a system according to the invention will now be described in greater detail with reference to FIG 1.

DESCRIPTION OF ILLUSTRATED EMBODIMENT

Figure 1:
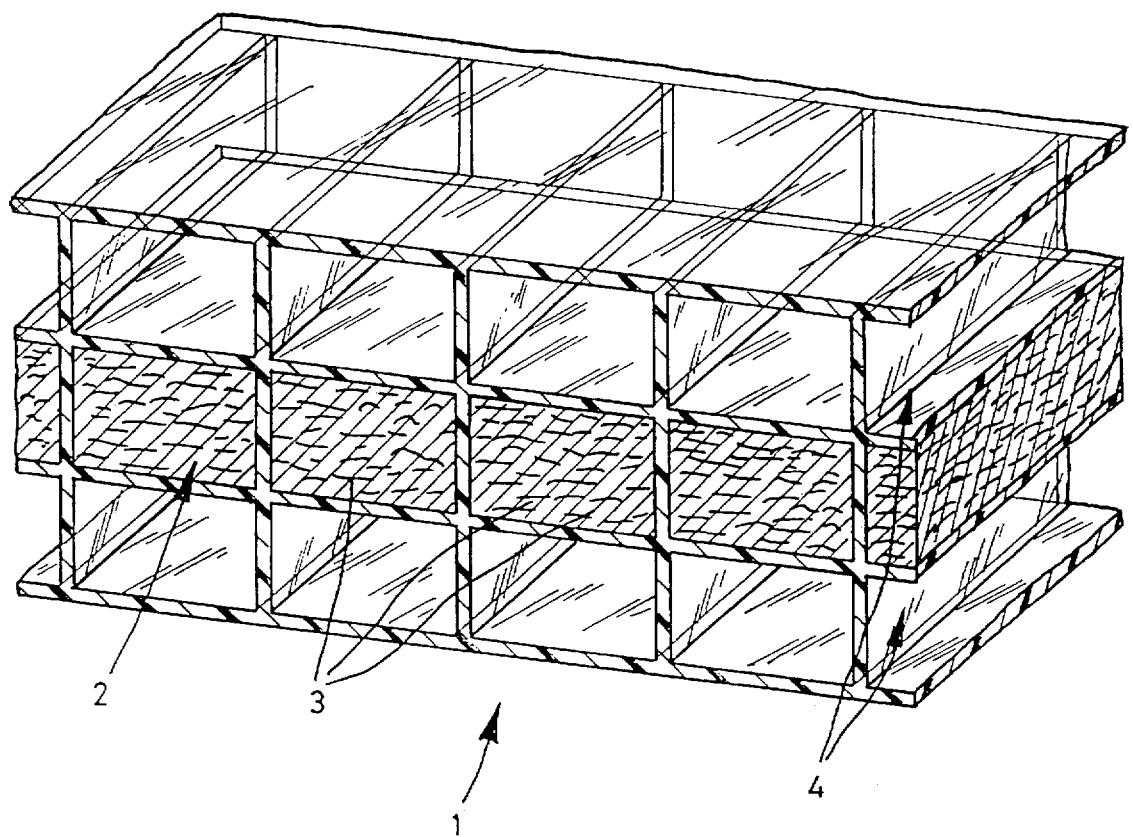

In FIG. 1 reference numeral 1 refers generally to a plane element designed as a three-layer ribbed plate. Plane element 1 has a middle layer 2 which, because of the ribs, consists of a plurality of individual channels 3. In middle layer 2, algae are pumped in the fluid through channels 3. Since the entire plane element 1 consists of a transparent material, polycarbonate for example, a suitable location of plane element 1 exposes the algae to daylight and permits conversion of the carbon dioxide contained in the fluid to oxygen.

Two outer layers 4 likewise consist of a plurality of channels. These outer layers 4 can be evacuated so that they acquire thermally insulating properties and protect the algae inside middle layer 2 from ambient temperatures. Under suitable temperature conditions, evacuation may also be eliminated, so that the entire system can be operated especially economically using plane element 1.

Plane element 1 as shown can be set up separately for example at an angle optimum for insolation. However, plane element 1 can also be used as a plane structural element, for covering light shafts or windows for example, with the two outer evacuatable layers 4 lending plane element 1 an outstanding insulating effect and contributing to an especially energy saving design, for example an air-conditioned or heated room.

In addition, in a design of plane element 1 that is not completely permeable to light, such a plane element 1 can be mounted directly on a building so that the insulating properties of plane element 1 improve the insulation of the structure and improve the energy balance for operating this building.

Particularly in production facilities, a surplus of energy is frequently available as a result of exhaust fumes, waste steam, or the like, which can be used to operate vacuum pumps to evacuate the two insulating layers 4.

The insulating effect of the three-layered embodiment described can also be achieved by combining a one- or two-layer plate with additional insulating layers, for example by mounting a plate with only one or two layers behind already existing windows or by a separate unconnected arrangement of single-layer plane elements, for example single-layer ribbed plates.

I claim:

1. A reactor vessel for processing gases containing carbon dioxide by means of a fluid containing algae comprising:
   a first elongated duct having a rectangular cross section with a top surface and a bottom surface for containing said gases and said fluid containing algae;
   a second elongated duct, abutting said first elongated duct, having a rectangular cross section with a top surface and a bottom surface, said duct having ribs extending from said bottom surface to said top surface to form a plurality of elongated channels for insulating said first elongated duct;
   wherein the channels of said second elongated duct are constructed so as to be evacuated to create a vacuum therein.

2. The reactor vessel of claim 1 wherein said top surface of said first and second ducts are permeable to light.

3. The reactor vessel of claim 1 wherein said first and second ducts are formed from a translucent material.

4. The reactor vessel of claim 1 wherein said first and second ducts are formed from a transparent material.

5. The reactor vessel of claim 1 wherein said first and second ducts are formed from polycarbonate.

6. A system for processing gases containing carbon dioxide by means of a fluid containing algae, said system comprising:
   a first elongated duct having a rectangular cross section with a top surface and a bottom surface for containing said gases and said fluid containing algae;
   a second elongated duct, abutting said first elongated duct, having a rectangular cross section with a top surface and a bottom surface, said duct having ribs extending from said bottom surface to said top surface to form a plurality of elongated channels for insulating said first elongated duct;
   a pump for evacuating the channels of the second duct to thermally isolate the first duct.

7. The system of claim 6 wherein said top surface of said first and second ducts are permeable to light.

8. The system of claim 6 wherein said first and second ducts are formed from a translucent material.

9. The system of claim 6 wherein said first and second ducts are formed from a transparent material.

10. The system of claim 6 wherein said first and second ducts are formed from polycarbonate.

* * * * *